United States Patent
Broadwell et al.

(10) Patent No.: US 12,130,279 B2
(45) Date of Patent: Oct. 29, 2024

(54) SYSTEMS AND METHODS FOR METER RECONFIGURATION, CONTROL, AND OPERATION VIA AN INSERTABLE CHIP WITH MICROPROCESSOR

(71) Applicant: POLYMER TECHNOLOGY SYSTEMS, INC., Whitestown, IN (US)

(72) Inventors: Jonathan A. Broadwell, Beech Grove, IN (US); James Miller, Indianapolis, IN (US)

(73) Assignee: Polymer Technology Systems, Inc., Whitestown, IN (US)

( * ) Notice: Subject to any disclaimer, the term of this patent is extended or adjusted under 35 U.S.C. 154(b) by 604 days.

(21) Appl. No.: 16/841,921

(22) Filed: Apr. 7, 2020

(65) Prior Publication Data

US 2020/0326326 A1 Oct. 15, 2020

Related U.S. Application Data

(60) Provisional application No. 62/831,567, filed on Apr. 9, 2019.

(51) Int. Cl.
*G01N 33/487* (2006.01)
*B01L 3/00* (2006.01)

(52) U.S. Cl.
CPC .. *G01N 33/48785* (2013.01); *B01L 3/502715* (2013.01); *B01L 2300/0654* (2013.01); *B01L 2300/0825* (2013.01)

(58) Field of Classification Search
None
See application file for complete search history.

(56) References Cited

U.S. PATENT DOCUMENTS

| | | | | |
|---|---|---|---|---|
| 5,366,609 A | * | 11/1994 | White | G01N 33/48792 435/817 |
| 2002/0082797 A1 | * | 6/2002 | Deweese | G01N 33/48785 702/122 |
| 2005/0279647 A1 | * | 12/2005 | Beaty | G01N 27/3272 205/792 |
| 2015/0050678 A1 | * | 2/2015 | Elder | C12Q 1/54 435/14 |
| 2015/0309010 A1 | * | 10/2015 | Furukawa | G01N 33/49 702/19 |
| 2015/0330988 A1 | * | 11/2015 | Ralston | G01N 27/416 600/583 |

FOREIGN PATENT DOCUMENTS

EP 0250243 A2 * 12/1987 ............ B01L 3/0206

* cited by examiner

*Primary Examiner* — Matthew D Krcha
(74) *Attorney, Agent, or Firm* — Haynes and Boone, LLP

(57) ABSTRACT

In one embodiment, a system for a configurable meter for analyte testing includes a meter, the meter configured to respond to commands in a first protocol and thereby control an analysis system for detecting an analyte level of an analyte, a display, and an input device. The system further includes a removable chip insertable into the meter, the removable chip configured to execute a protocol when mated with the meter and send the commands in the first protocol to control the meter, the removable chip further configured to calculate the analyte level as part of the protocol.

19 Claims, 6 Drawing Sheets

SYSTEMS AND METHODS FOR METER RECONFIGURATION, CONTROL, AND OPERATION VIA AN INSERTABLE CHIP WITH MICROPROCESSOR

CROSS REFERENCE

This application claims the benefit of U.S. provisional application No. 62/831,567, filed Apr. 9, 2019, the entirety of which is hereby incorporated by reference.

BACKGROUND

Diagnostic testing devices find usage in many scenarios, including home use, use by a doctor's office, and usage at health fairs. Diagnostic testing devices typically perform testing for various analytes in a bodily fluid and yield results that are equivalent to laboratory testing. In many scenarios, a meter may be used in concert with a test strip to detect an analyte level of a first analyte according to a first protocol. The first protocol may be matched with the specifics of the test strip. The meter may not be configurable after distribution to execute different protocols for the detection of other analytes. Therefore, it may be desirable to provide a meter system that is more readily configurable with a low chance for user error of misconfiguration.

BRIEF SUMMARY

In one embodiment, a system for detecting an analyte in a bodily fluid sample includes a meter, the meter including an analysis system, a display, and an input device. The system further includes a removable chip, the removable chip interfacing with the meter, the removable chip including a processor that executes an algorithm stored on a computer readable medium on the removable chip and controls the operations of the meter. The system further includes a test strip, insertable into the meter, the test strip configured to receive a sample when inserted in the meter, the meter configured, via the commands of the removable chip to use the analysis system to analyze the test strip and provide an analyte level in the sample. Alternatively, the removable chip does not include a power source and the meter provides power to the removable chip when inserted into the meter. In one alternative, the algorithm on the removable chip includes a testing protocol for the analyte level. In another alternative, the removable chip includes a memory device. In another alternative, the memory device includes a calibration curve for analysis of the analyte level, the calibration curve related to the test strip. Alternatively, the testing protocol is specific for the analyte tested for and different analytes have different testing protocols when using the meter. In another alternative, the processor of the removable chip controls the meter by sending commands to the meter according to a control language. Alternatively, the processor of the removable chip is configured to communicate with the meter using a control language. In another alternative, the meter is configured to control the analysis system, the display, and the input device according to commands received from the removable chip in the control language. Alternatively, the meter is configured to return signals reflective of the analyte level to the removable chip and the removable chip is configured to calculate the analyte level response to the signals. In another alternative, the meter is an optical meter. Alternatively, the bodily fluid is blood. Alternatively, analysis of the test strip only returns accurate results when used with a removable chip specific to the test strip. In another alternative, the removable chip includes calibration information specific to a lot that the test strip was produced as part of. Alternatively, the meter does not function properly without the removable chip.

In one embodiment, a method of testing for an analyte level in a blood sample includes providing a test strip, a meter, and a removable chip specific for the test strip. The method further includes inserting the removable chip in the meter. The method further includes inserting the test strip in the meter. The method further includes applying a blood sample to the test strip. The method further includes calculating a level of an analyte in the blood sample, the calculating occurring in the removable chip. The method further includes displaying the level of the analyte with the meter. In one alternative, the removable chip includes a processor. In another alternative, the removable chip is powered by the meter. Alternatively, the calculating includes executing a first protocol in the removable chip and thereby commanding the meter to analyze the test strip and return first output to the removable chip. In one alternative, the method further includes providing a second test strip and a second removable chip; inserting the second removable chip in the meter; inserting the second test strip in the meter; applying a second blood sample to the second test strip; calculating a second level of a second analyte in the second blood sample, the calculating occurring in the second removable chip; and displaying the second level of the second analyte with the meter. Optionally, the calculating includes executing a second protocol, the second protocol different from the first protocol, in the second removable chip and thereby commanding the meter to analyze the second test strip and return second output to the second removable chip.

In another embodiment, a system for a configurable meter for analyte testing includes a meter, the meter configured to respond to commands in a first protocol and thereby control an analysis system for detecting an analyte level of an analyte, a display, and an input device. The system further includes a removable chip insertable into the meter, the removable chip configured to execute a protocol when mated with the meter and send the commands in the first protocol to control the meter, the removable chip further configured to calculate the analyte level as part of the protocol. Optionally, the removable chip is associated with a test strip and the test strip is inserted into the meter. Alternatively, the protocol is specific to the test strip.

DETAILED DESCRIPTION

Figure 1A:
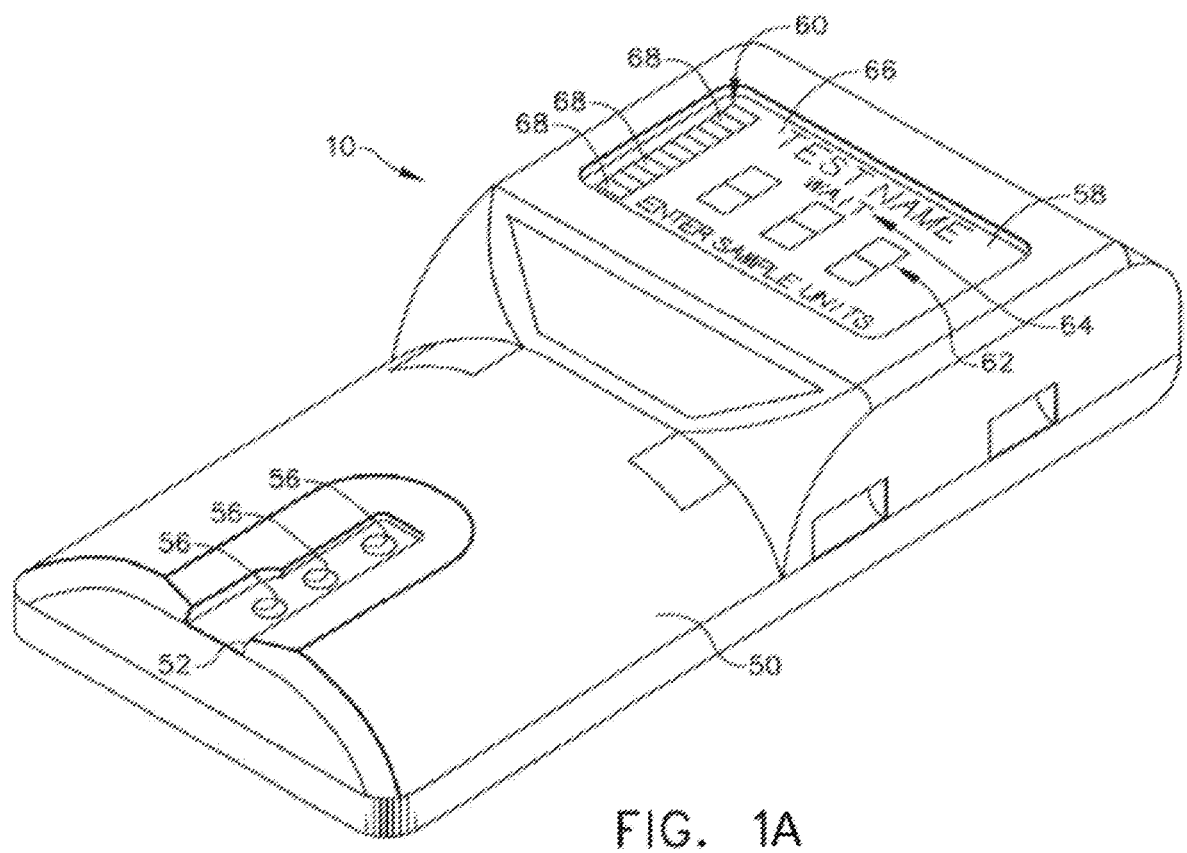
FIG. 1A shows one embodiment of a meter for use with systems and methods for meter reconfiguration, control, and operation via an insertable chip with microprocessor.

Certain terminology is used herein for convenience only and is not to be taken as a limitation on the embodiments of the systems and methods for meter reconfiguration, control, and operation via an insertable chip with microprocessor. In many embodiments a meter system is provide that receives a chip. The chip provides for reconfiguration and calibration of the meter. Therefore, the chip includes information, not only for the calibration curve of the strip, but information and algorithms for controlling the meter in various ways. Therefore, the meter has essentially a dual control system, with the meter including microprocessors for controlling the LEDs, the light detectors, and the screen of the device and a second microprocessor or microprocessors located in an insertable (removable) chip (hereinafter many times referred to as a PRoMEM chip) that controls the operation of the first microchip, and directly controls the algorithms, test execution sequence, user prompts, and conversion from measurements to clinical values that form part of the testing procedure. In other words, the meter microprocessor (generic herein for one or more microprocessors contained in the meter) provides for basic control algorithms for the device, however, does not provide a test sequence, algorithm for analysis, or directly supply sequences of prompts for the user. This programming is provided by and executed by the PRoMEM chip system. This allows for ease of post-sale configuration of the meters that the PRoMEM chip works with. The specific PRoMEM chips are typically matched by color with the test strip used with them, therefore reducing chance for user error of inserting the wrong chip and using the wrong protocol. In other words, test strips having a black holder are typically matched with PRoMEM chips having a black shell, test strips having a red holder are typically matched with PRoMEM chips having a red shell, etc. Typically, the test strips have a plastic holder that is easily colored and similarly, the PRoMEM chips have a similar plastic shell.

Therefore, in many embodiments, a meter is provided with a removal able/insertable control module (the PRoMEM chip). The PRoMEM chip provides and executes via its microprocessor the algorithm for operating the meter and the calibration information. The meter includes a microprocessor that enables the operation and retrieval of measurements from the LEDs and sensors. The microprocessor of the meter controls the user interface display as well.

Therefore, in one embodiment, the PRoMEM chip includes instructions for a test. The test instruction may include:

1. Prompting the user to insert a strip;
2. Prompting the user to confirm that the strip type matches the PRoMEM chip being used;
3. Prompting the user to dose the strip with a sample;
4. Activating an LED for a period of time;
5. Sensing, with sensors, reflectance of for activating an LED of the meter;
6. Determining when the test has operated for a sufficient length of time (in some cases this means determining when the readings have stabilized or the slope is consistent);
7. Calculating an analyte level based on the sensing;
8. Notifying the meter to display test results.

In this scenario, although the PRoMEM chip includes instruction for executing these commands, note that some of the commands/instruction will include the meter actually executing parts of the instructions. For instance, in #1, although the PRoMEM chip includes instructions for prompting a user to insert a strip, the way that the PRoMEM chip does so is through communicating with the microprocessor of the meter. In other words, the PRoMEM chip includes the algorithm for how the prompts should proceed and the microprocessor of the meter actual activates the graphics of the screen. In #2, when the PRoMEM chip continues to execute its algorithm and proceeds to prompt the user to indicate as before that the PRoMEM chip inserted matches the strip inserted. This is typically performed by the PRoMEM chip sending instructions to the microprocessor of the meter indicate what type of instructions to display. In this scenario, the microprocessor of the meter then actually triggers the display on the meter screen. In #3, the PRoMEM chip continues to execute its algorithm with its processor, causing it to prompt the user to dose the strip. The PRoMEM chip does so by sending instructions to the processor of the meter, thereby causing the meter to display the corresponding instructions. In #4, the PRoMEM chip continues to execute its algorithm, and the PRoMEM chip processor reads instructions resident on the PRoMEM chip for how long to activate at least one LED for reading the inserted strip. The PRoMEM chip then sends instruction to the meter to activate the LED and times the activation of the LED to run for the test period, thereby running a test on the strip after the strip is dosed. In relation to #5, the PRoMEM chip communicates with the processor of the meter in order to receive reflectance measurements from one or more reflectance sensors of the meter. Based on this in #6 and 7 the PRoMEM chip executes code to determine what the analyte level is. Finally, in #8 the PRoMEM chip causes the meter to display the results to the meter.

Although this methodology has been described in relation to a specific meter and PRoMEM chip combination, meters with varying characteristics may be utilized. Essentially, in many scenarios, the PRoMEM chip contains the instructions for executing testing and the microprocessor for executing the testing. The meter contains an interface for a user, a display, and a testing mechanism, which may consist of various sensors and excitation generators (such as a voltage source, an amperage source, a light source, a heat source). The meter contains mechanisms and processors for actually controlling these pieces of the device. In operation, the PRoMEM chip executes its algorithm and 1) causes various instructions and results to be displayed to the user by communicating with the processor of the meter which these effectuates the display of the instructions, results, or other information; 2) receives various input via the interface and the processor of the meter that are then communicated to the PRoMEM chip for processing; and 3) interrogates the test strip via the testing mechanism and processor of the meter. In this way, the PRoMEM chip may mate with and control the meter to perform testing procedures. Additionally, this may offer additional flexibility for what tests may be run on a particular meter. For instance, two somewhat different meters may be utilized to perform the same type of testing by enabling the PRoMEM chip to detect the type of meter it has been inserted into and to conduct the testing according to that meter by providing somewhat different testing procedures that account for the differences between meters.

By way of example, it is useful to describe a system in which the PRoMEM chip with processor may operate. Note that in many scenarios, it is called a PRoMEM chip, but it may also be referred to an unpowered removable memory device and processor combination, a removable unpowered chip, a removable chip with processor that interfaces with a meter having a separate processing system. Although in many scenarios, the PRoMEM chip is described as being unpowered, this is not necessary in all scenarios. In many embodiments, a split processor system is utilized. This system provides for a configured meter, that controls an interface, a display, and a sensing mechanism that includes a processing system that can receive commands from another source and thereby control the interface, display, and sensing system and communicate resultant data and inputs to the PRoMEM chip. It is this PRoMEM chip (or removable chip with processor and memory) that provides commands to the meter and decides what steps to employ. An objective of the system is to control the meter in order to use the inserted test strip to detect an analyte in a bodily fluid.

In accordance with an embodiment of a meter or analyzer such as a PRoMEM chip, analyzer, and test strip combination, photometric device 10 as shown in FIG. 1A includes a hand-held housing 50 for containing electronic control circuitry for operating analyte tests. In the embodiment shown in FIG. 1A, a test strip holding region 52 is located above three light detectors or sensors 54 each disposed within a port 56. During test operation, a test strip 12 is inserted into holding region 52 so that test strip openings 26 are located adjacent ports 56. Light sensors may take a reading from light reflected from the exposed test reaction membrane layer 32 or from test strip 12 itself to determine its color.

Housing 50 further includes a specialized display device, such as a liquid crystal display 58. Display 58 is utilized for relating test results and other information to the user. In particular, a color scale 60 may be used to facilitate interpretation of test results operating concurrently with digital display segments 62. Additional display segments on display 58 include a test wait indicator segment 64 to inform the user to wait while device 10 is performing the selected tests, and a test name segment 66 which the unit determined from the type of test strip 12 inserted. This is merely an example of one analyzer.

Color scale 60 may easily by constructed by a plurality of shaded or colored segments arranged adjacent each other to form a bar graph like indicator. Electrically controllable segments 68 are oriented over the color or shaded segments so that when segments 68 are activated segments 68 become dark, preventing certain colored or shaded segments 60 from being visualized or viewed. Segments 68 that are not activated permit the underlying colored or shaded segments of color scale 60 to be visualized. In this way it is possible for an electronic control to permit only a single colored or shaded segment to be viewed thereby communicating test results.

Figure 1B:
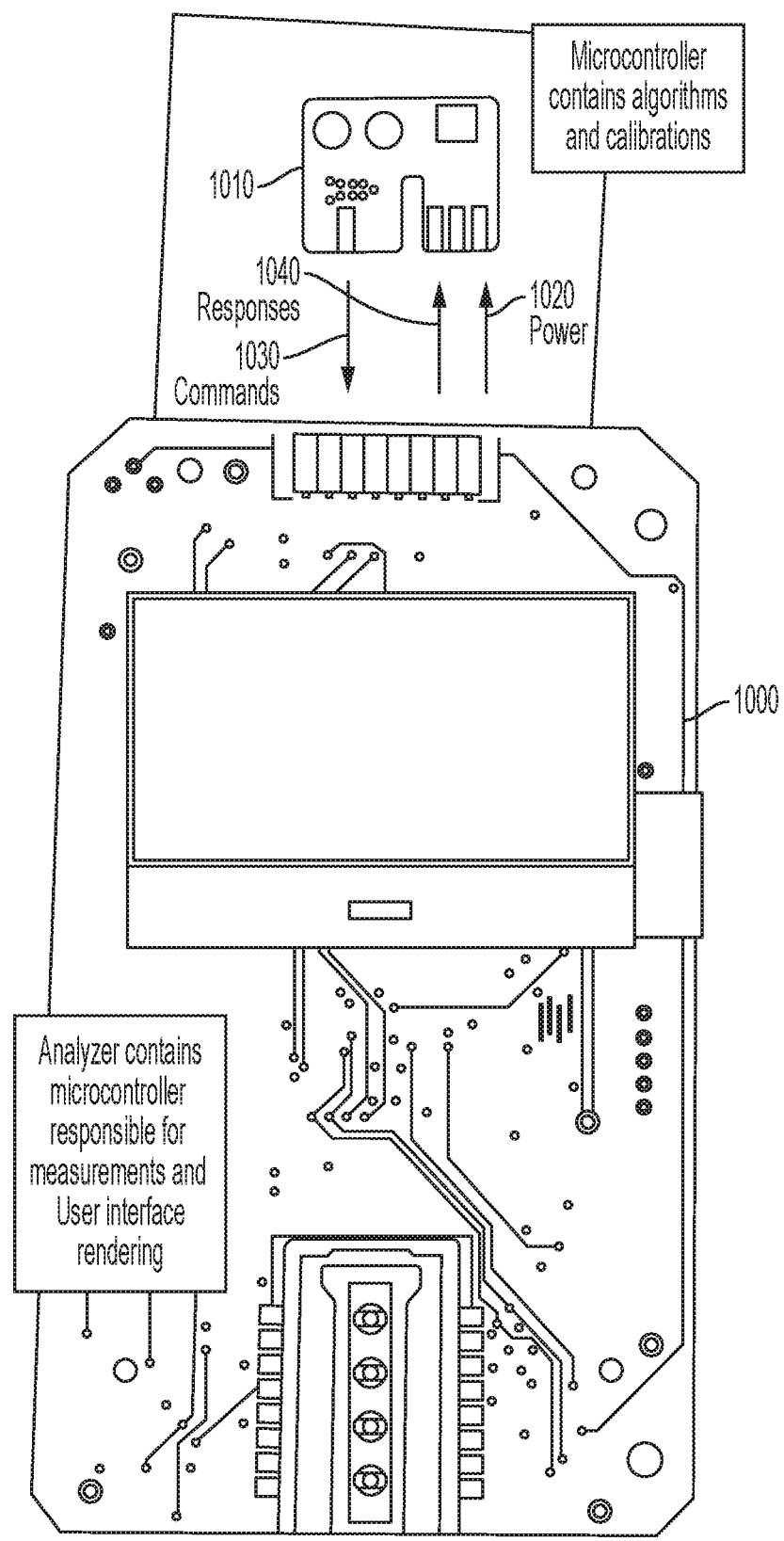
FIG. 1B shows the meter of FIG. 1 with the cover removed and the insertable chip without a cover.

As shown in FIG. 1B, the PRoMEM chip 1010 is insertable into meter 1000 (shown with the cover removed). In operation the meter 1000 (meter 10) provides power to the PRoMEM chip 1010 which includes leads for the transfer of power 1020. PRoMEM chip 1010 also includes a microprocessor and memory. PRoMEM chip sends commands 1030 to the meter and controls it according to the test to be run. Meter 1000 provides responses back to PRoMEM chip 1010.

In many embodiments, a test strip for blood analyte detection is made up of a molded carrier test strip 20 in which several porous and nonporous materials containing chemicals and reactants are contained for the purpose of generating a detectable signal in the presence of certain analytes. The test strip 12 is inserted into the meter, which is a reflectance photometer. The reaction material layer on the test strip 12 produces an indication of an analyte.

Figure 2:
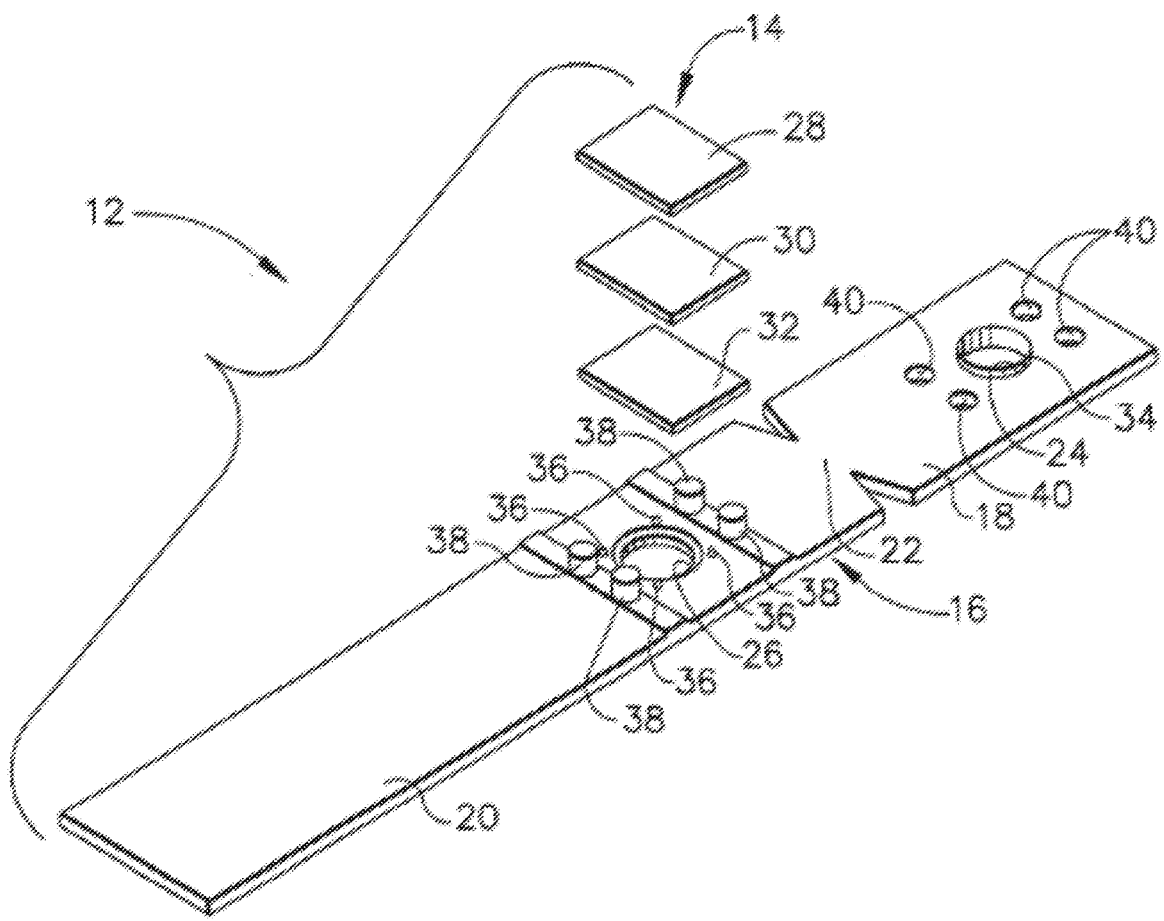
FIGS. 2-4 shows various views of a test strip for use with the meter and insertable chip with microprocessor combination.

The holder of test strip 12 acts as holder for the different layers of the test reaction system. It provides a convenient handle as well as a mechanism for placing test strip 12 into an instrument 10 for the reading of the changes of indications such as a color change or a reflectance change. As shown in FIG. 2 test strip 12 includes an elongate body 16, which may be formed by injection molding. Elongated body 16 includes a first end portion 18 and a second end portion 20. A hinged portion 22 is located between first and second end portions 18 and 20 so that first end 18 is foldable over elongated body 16 into contact with second end 20. This is only one possible configuration for the test strip and various aspects may be changed including the structure of the body, the type of test strip, etc.

Figure 3:
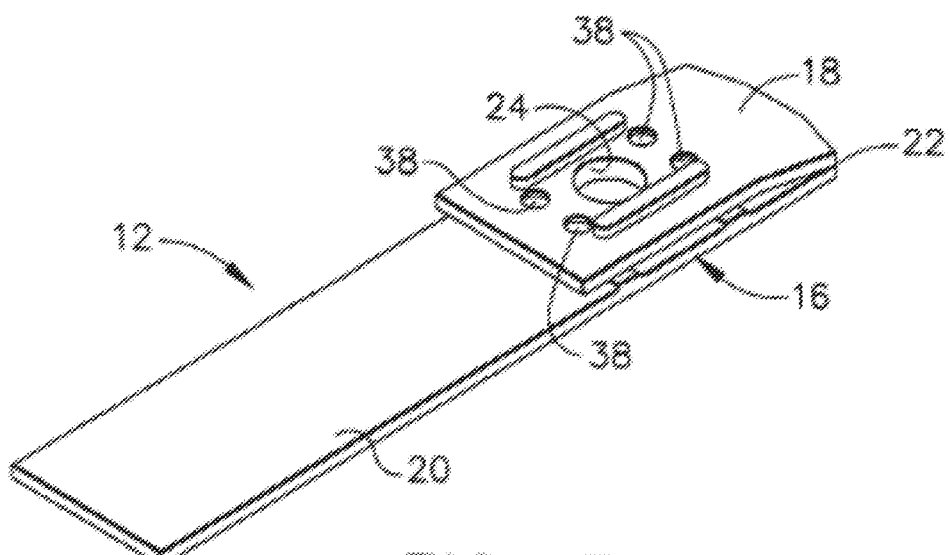
Figure 4:
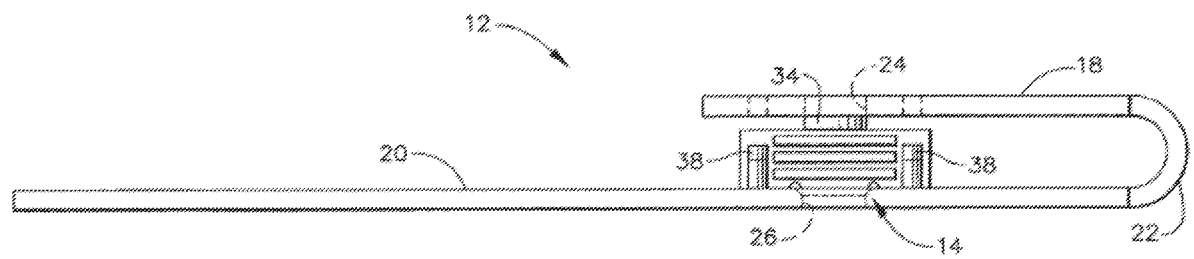

As shown in FIG. 2 first end portion 18 includes a opening 24 while second end portion 20 includes a complementary spaced opening 26. When first end portion 18 is folded over body 16, each opening 24 and 26 are aligned. In its folded position as shown in FIG. 3 opening 24 in test strip 12 defines an area for depositing a body fluid sample while opening 26 defines an area in which optoelectronic measurements of chemistry test reactions are conducted. In alternative embodiments, test strips with multiple apertures may be used as well as different types of test strips, such as electrochemical.

Test strip 12 further includes a carrier layer 14 formed from, for example, three layers. In a standard diagnostic test strip, carrier layer 14 may include a disbursement layer 28, formed of for example woven materials such as polyester or cotton, for rapid and even disbursement of body fluid along carrier layer 14. Beneath that may be included a separating layer 30 that, when exposed to a sample liquid, may separate analyte and analyte disrupting elements such as red blood cells from whole blood. This action would permit the serum analytes to pass through separating layer 30 while preventing red blood cells or other analyte disrupting elements from passing through. The last layer shown in FIG. 2 is that of the test reaction membrane 32 on which the dry chemicals and reactants are contained for generating a visible signal in the presence of serum analytes. Molded carrier body 16 serves as a support for the reacting and nonreacting layers 28, 30 and 32 which may be formed from various membranes and layers. More layers may be used.

The test strip holder 12 positions the different layer materials 28, 31, 32 within the holder the correct X, Y, and Z axis positions. Carrier layer 14 made up, for example, the disbursement separating and test reaction layers 28, 30 and 32 are held in location by first end portion 18 folding over to second end portion 20.

Test strip 12 may include a locking mechanism to prevent any unlocking of front end portion 18 from its folded position over elongated body 16. As shown in FIG. 2, one type of locking mechanism may include a plurality of upwardly extending tabs or projections 38 that interfit or lock into corresponding openings 40 in first end portion 18. When first end portion 18 is folded to second end portion 20, lock projections 38 will interfit and snap lock within openings 40. Other types of one way locking mechanisms may also be used, such as snap rivets.

More than one test reaction system can be housed in a test strip 12. A second set of holes 24, and 26 may be included in test strip 12 so that two tests may be run at once.

The described holding mechanism allows for the rapid separation of whole blood into its liquid and solid components. Chemicals and materials are employed to allow for the treatment of samples such as whole blood, which will allow the whole blood sample to be separated while rapidly moving the liquid portion of the whole blood sample to one or more reaction sites in the holder, normally on a test reaction membrane 32. The materials which may be used in the holder for treatment by or containment of these chemicals can be composed of woven, nonwoven, napped, or flocked materials.

Figure 5:
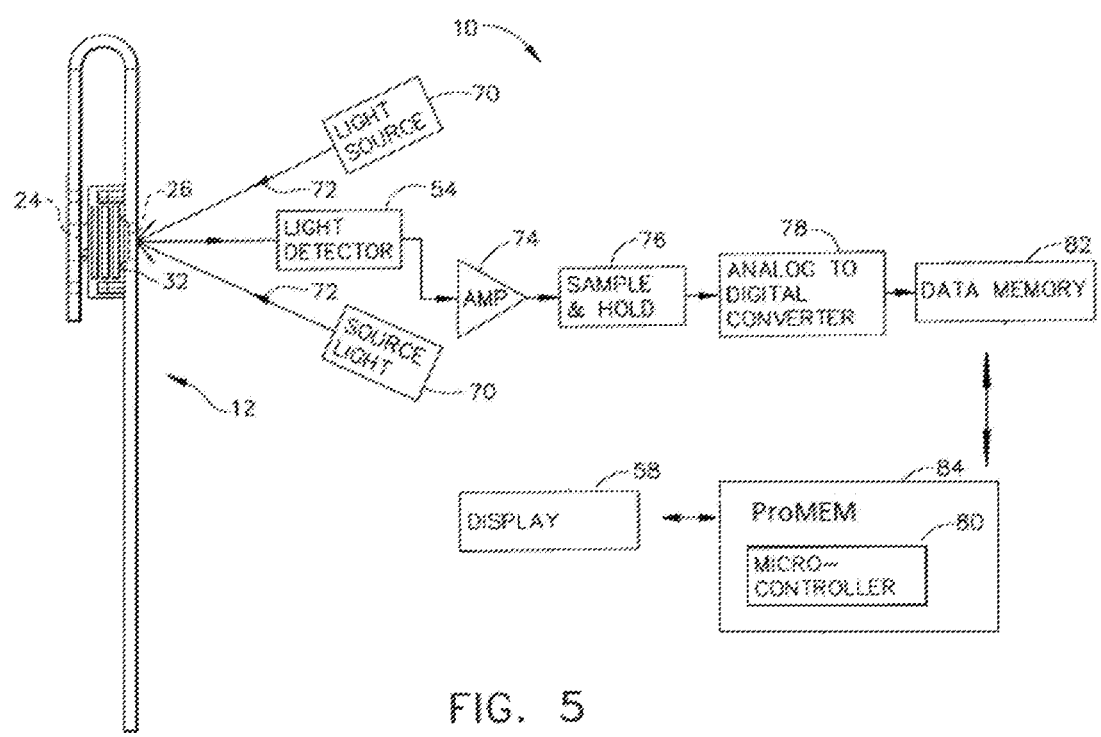
FIG. 5 shows a schematic of operation of the meter and insertable chip with microprocessor.

A suitable instrument, such as a diffuse reflectance spectrophotometer 10 (also known as a meter), and with the addition of the PRoMEM chip which includes appropriate software that cause the meter 10 to automatically read reflectance at certain points in time, while the PRoMEM chip calculates the rate of reflectance change, and by using calibration factors and software and output the level of analyte in the fluid tested received from the meter. The electronic control mechanism of photometric unit 10 is shown in schematic form in FIG. 5. One or more light sources 70, for example high intensity light emitting diodes (LED) are disposed in housing 50 to illuminate test strip 12 as shown by arrows 72. A light detector or sensor 54, for example a photo transistor, is able to take a reading of light reflected either from the surface of test strip 12 or from its associated test reaction membrane 32. Light source 70 and light sensor 54 can be adapted to generate or respond to particular wavelengths of light.

Sensor 70 transmits a signal to an amplifier 74 as is known in the art. One type of amplifier available for use is, for example, a linear integrated circuit which converts the phototransistor current to a voltage signal.

Appropriate electronic Circuitry is utilized to take the output of amplifier 74, normally a sample and hold unit 76, and transfer the signal to an analog-to-digital converter 78. Analog-to-digital converter takes the analog voltage output from the sample and hold unit 76 and converts it to, for example a 16-bit binary digital number upon command of a microprocessor/microcontroller unit 80.

In many embodiments, a meter-based microprocessor/microcontroller utilizing digital integrated circuitry is used to control the display, input devices, and analysis systems (LED and detector) of the meter, however, this is all at the command and analysis of the PRoMEM chip. The meter-based system may include a memory 82 for temporarily storing output before transferring to the PRoMEM chip unit 84.

Additional information for particular tests may be stored in a removable PRoMEM chip 84 which includes microprocessor/microcontroller 80. Microprocessor/microcontroller 80 contains and executes the test programming as described herein. PRoMEM chip unit 84 is an interchangeable plug-in memory module containing measurement parameters, software, calibration data, and reagent recognition data for particular test strips 12. Additionally, PRoMEM chip unit 84 contains the shelf life data and identity verification information for particular production runs or lots of test strips 12. Additionally, as indicated above, PRoMEM chip includes a microprocessor that commands the meter, calculates the rate of reflectance change and output the analyte level to the meter and commands the meter to display it. In many embodiments, PRoMEM chip is powered by the meter and does not include a power source.

Many current systems only provide calibration information via an insertable memory device, such as the MEMo chip system in the CardioChek devices. This limits the flexibility of the system to run new assays unanticipated at the time of manufacture of the analyzer due to the need for pre-loaded algorithms for test execution and conversion of physical measurements into clinically applicable In contrast to prior systems, an entire microcontroller is contained within the PRoMEM chip shipped with each lot of consumable test supplies allowing both calibration and test execution to vary by lot.

New or existing assays can have their algorithms, test execution sequence, user prompts, and conversion from measurements to clinical values change on a lot-by-lot basis. This allows introduction of new assays without the need to update prior firmware stored in the analyzer to run new algorithms. Prior solutions limited new assays to existing algorithms if they are to be run on analyzers already in the field. Since the entire algorithm is stored in the new PRoMEM chip type, these limitations are eliminated.

An inexpensive microcontroller is mounted to a PCB board which is inserted into a port on the analyzer by an end user when a given lot of consumables is used. This microcontroller contains software code which implements an algorithm which directs the analyzer into which is inserted to carry out commands. These commands may drive user-interface interaction, physical measurement, or other algorithm related tasks such as requesting the Analyzer's version, serial number, or real-time clock value. Firmware in the analyzer processes and responds to these requests. In the case that each lot requires specific calibration constants, these can be stored in the PRoMEM chip as well.

A communication protocol is defined for interaction between the PRoMEM chip and analyzer/meter. In one embodiment, a UART (Universal Asynchronous Receiver/Transmitter) communication method is used, with a proprietary data protocol running on top. This protocol includes a CRC algorithm (cyclic redundancy check) to help ensure uncorrupted communication. A scheme of acknowledgements and retries are provided to help ensure reliable communication.

Figure 6:
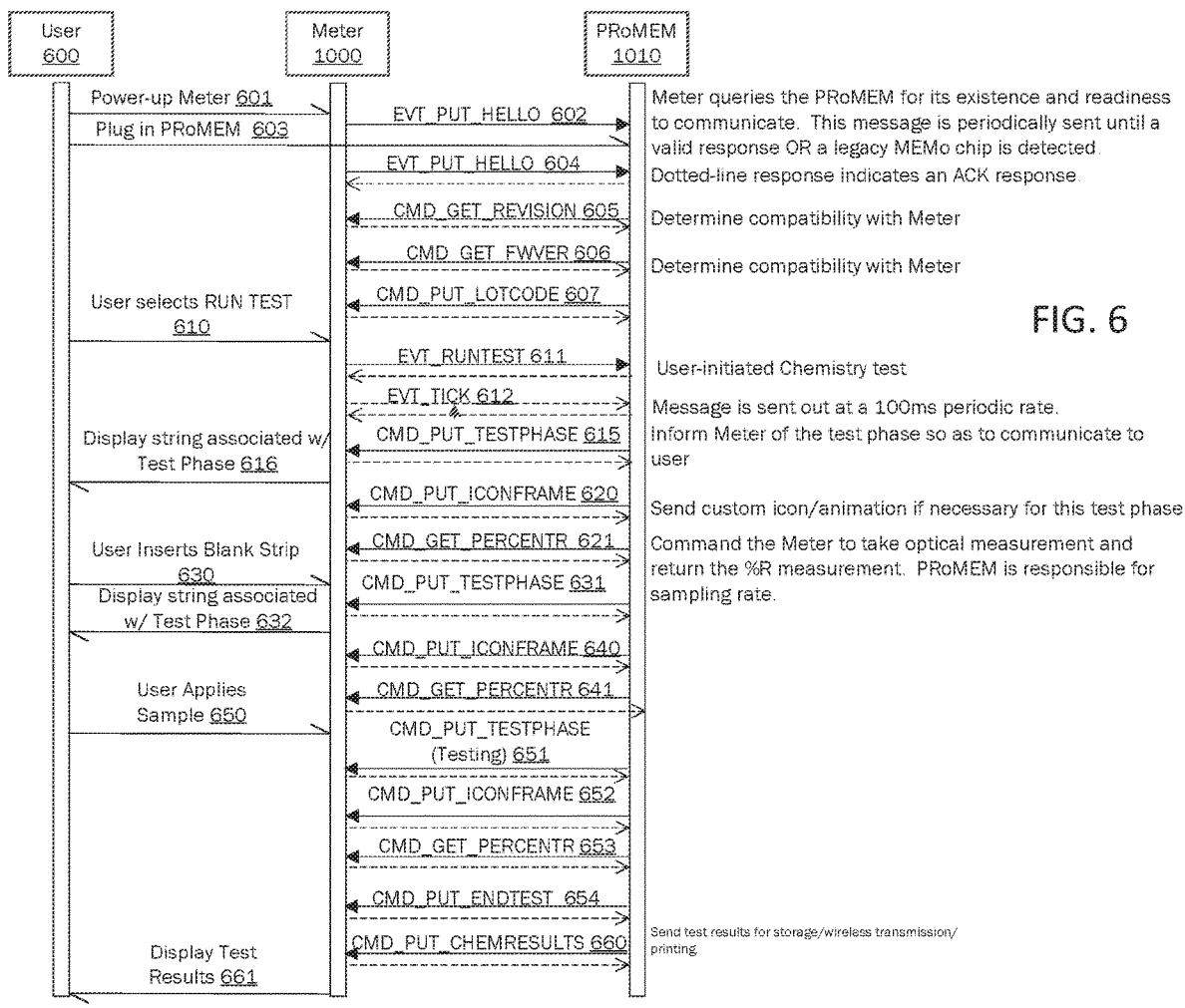
FIG. 6 shows one embodiment a sequence diagram for operation of the meter and insertable chip with microprocessor.

FIG. 6 shows one embodiment a sequence diagram for operation of the meter and insertable chip with microprocessor. FIG. 6 shows a user 600, a meter 1000, and the PRoMEM 1010. First, user 600 powers up the meter in communication 601. This typically occurs by pushing or actuating a button or switch. Then meter 1000 queries to determine if and what type of chip has been inserted into the meter in EVEN_PUT_HELLO 602. This may continually and periodically occur. In communication event 603, the user may plug in the PRoMEM 1010 to the meter 1000. In EVENT_PUT_HELLO 604, the PRoMEM chip has been inserted so the PRoMEM 1010 returns an acknowledgement message denoted by the dotted line. In CMD_GET_REVISION 605, the PRoMEM 1010 requests the meter 1000 version status and other information to help determine whether it is compatible with the meter. The dotted line denotes the response from the meter. In CMD_GET_FWVER 606, the PRoMEM 1010 requests the firmware version of the meter 1000. Other information concerning the meter's status may be requested in some embodiments. In CM_PUT_LOTCODE 607, the PRoMEM 1010 may provide the lot code of the PRoMEM 1010 and the associated strips. In communication 610, the user 600 selects from the interface on the meter 1000 that a test is to be run. The meter 1000 communicates EVT_RUNTEST 611 to PRoMEM 1010 denoting that a test is to be run. The PRoMEM 1010 then sends EVT_TICK 612, denoting what the message rate is to be, in this case 100 ms periodically. PRoMEM 1010 then sends a CMD_PUT_TESTPHASE 615 message to the meter 1000. Responsively, the meter 1000 displays an associated text string via the display of the meter 1000 in communication 616.

Then the PRoMEM 1010 may send a custom icon for display via CMD_PUT_ICONFRAME 620 on the meter 1000 during testing. Then the PRoMEM 1010 sends CMD_GET_PERCENTR 621 communication/command in order to command the meter 1000 to take optical measurement and return the % R measurement in order to detect, via a change in reflectance, when the strip is inserted. PRoMEM is responsible for sampling rate. Then the user inserts a blank test strip 630. Subsequently, PRoMEM 1010 sends the command CMD_PUT_TESTPHASE 631 which cause meter 1000 to display a text string instruction the user to apply a sample 632. Then, PRoMEM 1010 instructs the meter via CMD_PUT_ICONFRAME 640 to display an apply sample icon. Then the PRoMEM 1010 sends CMD_GET_PERCENTR 641 communication/command in order to command the meter 1000 to take optical measurement and return the % R measurement to establish a baseline reflectance reading. Then the user 600 applies a sample 650. The PRoMEM 1010 then sends CMD_PUT_TESTPHASE (Testing) 651 and the meter 1000 continues to monitor the strip. Then, PRoMEM 1010 instructs the meter via CMD_PUT_ICONFRAME 652 to display a testing icon. Then the PRoMEM 1010 sends CMD_GET_PERCENTR 621 communication/command in order to command the meter 1000 to take optical measurement and return the % R measurement in order to determine when the change in reflectance reaches an endpoint. Then, PRoMEM 1010 instructs the meter via CMD_PUT_ENDTEST 654 to end the test and display that it has ended. Based on the reflectance measured, the PRoMEM 1010 then calculates the test results/analyte level. Then, PRoMEM 1010 instructs the meter via CMD_PUT_CHEMRESULTS 660 to display the test results. Subsequently, the meter displays the test results 661. Note that is merely an example of one logic that may be used in the PRoMEM/meter combination and an example of commands that may be used. Many other configurations may occur.

Please note that the system herein is described in terms of optical tests. In many embodiments, the PRoMEM/meter system may be employed in electrochemical type tests. In some embodiments, the systems use this scheme on the CC+ hardware and addition of this micro-on-a-chip functionality. In some embodiments, the meter itself includes an electrochemical test strip slot. In some embodiments, the PRoMEM may include the test strip or a slot for the test strip itself. In this configuration, the PRoMEM may be an insertable microprocessor system that also includes a port for receiving a sample and electrodes to measure an analyte in that sample. In this configuration, the PRoMEM includes the parts described in many other embodiments herein and in addition the port and electrodes (typically coated with a reagent) for measuring the analyte. Additionally, in some embodiments, the PRoMEM may both run the optical components of the meter and have the port and electrodes (typically coated with a reagent) for measuring an additional analyte, not via the strip inserted into the meter, but electrochemically. Therefore, a strip may be inserted to be measured optically, and test for (for example) a lipid panel of HDL, TRIGS, and Total Cholesterol, while the integrated electrochemical port and electrodes in the PRoMEM, test for glucose. In many cases, the PRoMEM would include the instructions, calibration, and processor for testing for all of these analytes.

In many embodiments, parts of the system are provided in devices including microprocessors. Various embodiments of the systems and methods described herein may be implemented fully or partially in software and/or firmware. This software and/or firmware may take the form of instructions contained in or on a non-transitory computer-readable storage medium. Those instructions then may be read and executed by one or more processors to enable performance of the operations described herein. The instructions may be in any suitable form such as, but not limited to, source code, compiled code, interpreted code, executable code, static code, dynamic code, and the like. Such a computer-readable medium may include any tangible non-transitory medium for storing information in a form readable by one or more computers such as, but not limited to, read only memory (ROM); random access memory (RAM); magnetic disk storage media; optical storage media; a flash memory, etc.

Embodiments of the systems and methods described herein may be implemented in a variety of systems including, but not limited to, smartphones, tablets, laptops, and combinations of computing devices and cloud computing resources. For instance, portions of the operations may occur in one device, and other operations may occur at a remote location, such as a remote server or servers. For instance, the collection of the data may occur at a smartphone, and the data analysis may occur at a server or in a cloud computing resource. Any single computing device or combination of computing devices may execute the methods described.

In various instances, parts of the method may be implemented in modules, subroutines, or other computing structures. In many embodiments, the method and software embodying the method may be recorded on a fixed tangible medium.

While specific embodiments have been described in detail in the foregoing detailed description, it will be appreciated by those skilled in the art that various modifications and alternatives to those details could be developed in light of the overall teachings of the disclosure and the broad inventive concepts thereof. It is understood, therefore, that the scope of this disclosure is not limited to the particular examples and implementations disclosed herein but is intended to cover modifications within the spirit and scope thereof as defined by the appended claims and any and all equivalents thereof.

What is claimed as new and desired to be protected by Letters Patent of the United States is:

1. A system for detecting an analyte in a bodily fluid sample, the system comprising:
    a meter, the meter including an analysis system, a display, and an input device, the meter including a meter microprocessor;
    a removable chip, the removable chip interfacing with the meter microprocessor, the removable chip including a processor that executes an algorithm stored on a non-transitory computer readable medium on the removable chip and controls the operations of the meter;
    a test strip, insertable into the meter, the test strip configured to receive a sample when inserted in the meter, the meter configured, via the commands of the removable chip, where the removable chip is programmed and the commands are executing on the processor of the removable chip, to use the analysis system to analyze the test strip and provide an analyte level in the sample, the removable chip and the meter communicating using a communication protocol.

2. The system of claim 1, wherein the removable chip does not include a power source and the meter provides power to the removable chip when inserted into the meter.

3. The system of claim 1, wherein the algorithm on the removable chip includes a testing protocol for the analyte level.

4. The system of claim 3, wherein the removable chip includes a calibration curve for analysis of the analyte level, the calibration curve related to the test strip.

5. The system of claim 4, wherein the testing protocol is specific for the analyte tested for and different analytes have different testing protocols when using the meter.

6. The system of claim 4, wherein the processor of the removable chip controls the meter by sending commands to the meter according to a control language.

7. The system of claim 6, wherein the meter is an optical meter.

8. The system of claim 4, wherein the processor of the removable chip is configured to communicate with the meter using a control language.

9. The system of claim 8, wherein the meter is configured to control the analysis system, the display, and the input device according to commands received from the removable chip in the control language.

10. The system of claim 9, wherein the meter is configured to return signals reflective of the analyte level to the removable chip and the removable chip is configured to calculate the analyte level response to the signals.

11. The system of claim 8, wherein the bodily fluid is blood.

12. The system of claim 1, wherein analysis of the test strip only returns accurate results when used with a removable chip specific to the test strip.

13. The system of claim 12, wherein the removable chip includes calibration information specific to a lot that the test strip was produced as part of.

14. The system of claim 1, wherein the meter does not function properly without the removable chip.

15. The system of claim 1, wherein the removable chip drives an electronic control mechanism of the analysis system.

16. The system of claim 15, wherein the electronic control mechanism is a photometric unit.

17. A system for configuring meters for analyte testing, comprising:
a meter, the meter configured to respond to commands in a first protocol and thereby control an analysis system for detecting an analyte level of an analyte, a display, and an input device, the analysis system part of the meter, the meter including a meter microprocessor;
a removable chip insertable into the meter, the removable chip and the meter communicating using a communication protocol, the meter querying what type of removable chip has been inserted into the meter, the removable chip configured to execute a protocol stored on a non-transitory computer readable medium when mated with the meter and send the commands in the first protocol to control the meter, the removable chip further configured to calculate the analyte level as part of the protocol, where the removable chip is programmed and the commands are executing on the processor of the removable chip to request a firmware version from the meter microprocessor to the removable chip to determine compatibility.

18. The system of claim 17, wherein the removable chip is associated with a test strip and the test strip is inserted into the meter.

19. The system of claim 18, wherein the protocol is specific to the test strip.

* * * * *